US00RE38150E

(19) United States
(12) Reissued Patent
Greatbatch et al.

(10) Patent Number: US RE38,150 E
(45) **Date of Reissued Patent: *Jun. 24, 2003**

(54) WICK-BASED LIQUID EMANATION SYSTEM WITH CHILD-RESISTANT OVERCAP

(75) Inventors: Keith J. Greatbatch, Finchampstead (GB); Mark E. Wefler, Racine, WI (US)

(73) Assignee: S. C. Johnson & Son, Inc., Racine, WI (US)

( * ) Notice: This patent issued on a continued prosecution application filed under 37 CFR 1.53(d), and is subject to the twenty year patent term provisions of 35 U.S.C. 154(a)(2).

(21) Appl. No.: 09/875,172

(22) Filed: Jun. 7, 2001

Related U.S. Patent Documents

Reissue of:
(64) Patent No.: 5,909,845
Issued: Jun. 8, 1999
Appl. No.: 08/673,393
Filed: Jun. 28, 1996

(51) Int. Cl.[7] ..... A24F 25/00
(52) U.S. Cl. ..... 239/44; 239/46
(58) Field of Search ..... 239/44–47, 55, 239/57

(56) References Cited

U.S. PATENT DOCUMENTS

| | | | | | |
|---|---|---|---|---|---|
| 1,586,044 | A | * | 5/1926 | Reed | 239/44 |
| 2,930,063 | A | * | 3/1960 | Stull | |
| 3,083,858 | A | * | 4/1963 | Biedenstein | |
| 3,724,756 | A | * | 4/1973 | Maltenfort | 239/47 |
| 4,496,307 | A | * | 1/1985 | Ginardi | 431/34 |
| 4,520,431 | A | * | 5/1985 | Fanelli et al. | 362/180 |
| 4,739,928 | A | * | 4/1988 | O'Neil | 239/45 |
| 4,757,911 | A | * | 7/1988 | Larkin et al. | |
| 4,915,301 | A | * | 4/1990 | Munteanu | 239/45 |
| 5,077,102 | A | * | 12/1991 | Chong | 239/44 |
| 5,121,859 | A | * | 6/1992 | Stull | |
| 5,201,440 | A | * | 4/1993 | Gross | |
| 5,249,695 | A | * | 10/1993 | Luch et al. | |
| 5,437,410 | A | * | 8/1995 | Babasade | 239/45 |
| 5,622,314 | A | * | 4/1997 | Eason | 239/44 |

FOREIGN PATENT DOCUMENTS

| | | | | |
|---|---|---|---|---|
| AU | 664685 | * | 11/1995 | |
| EP | 0740941 A1 | * | 11/1996 | |
| FR | 688320 | * | 1/1930 | 239/47 |
| FR | 747069 | * | 2/1932 | 239/44 |
| IT | 477291 | * | 12/1953 | 239/47 |

* cited by examiner

*Primary Examiner*—Michael Mar
*Assistant Examiner*—Dinh Q. Nguyen

(57) ABSTRACT

A child-resistant, wick-based liquid emanation system includes a container which is capable of containing liquid and has an opening. A wick is partially disposed within the container and extends through the opening of the container. A hollow overcap encases the extended portion of the wick and has a closed, separable tip and an open base attached to cover the opening of the container. The system is activated by separating the tip from the overcap. A retainer may be provided for obstructing complete removal of the wick from the container through the overcap after the tip is separated from the overcap. The retainer can include a shoulder disposed in the overcap between the tip and the base to retain the wick toward the base of the overcap. Alternatively, a protrusion from the wick can engage an inner surface of the overcap or the container. In this case, the overcap can have a frangible portion facilitating separation of the tip, and the wick can extend past the frangible portion toward the tip.

44 Claims, 4 Drawing Sheets

WICK-BASED LIQUID EMANATION SYSTEM WITH CHILD-RESISTANT OVERCAP

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to wick-based liquid emanation systems, and more particularly to (i) a wick-based liquid emanation system having a child-resistant overcap, and (ii) a child-resistant overcap for use with the wick-based liquid emanation system.

2. Description of the Related Art

Wick-based liquid emanation systems are known in the art for dispersing into the air vaporized particles of any number of liquids. Such systems are often used in the home with liquids varying from insect repellent to air freshener. Typically, in such systems, one end of a wick is partially submerged in the liquid to be dispersed. The liquid is contained in any suitable container. The partially submerged portion of the wick absorbs the liquid, some of which diffuses by capillary or wicking action into the exposed, unsubmerged portion of the wick. The exposed portion of the wick is locally heated, often by means of a ring-shaped heater which fits over the wick. This causes the liquid which has diffused into the exposed portion of the wick to molecularize or evaporate into the surrounding air. Continual application of heat to the exposed portion of the wick results in an evaporation/absorption process that continues until the liquid is consumed.

A problem with conventional wick-based liquid emanation systems, as with many products suitable for home use, is the potential that a child will come into contact with the liquid contents of the system. For example, this can occur when the child tampers with the system or if the system is accidentally tipped over, the contents spilled and left for the child to discover. Many of the liquids utilized with such systems can be harmful if ingested, and some are harmful if merely contacted. Therefore, it is desirable to make these systems "child-resistant" and "spill-resistant" to reduce the chance that a child will access the potentially harmful contents of the system.

An additional concern is the potential that the contents of the system will be prematurely lost through spillage or evaporation. Therefore, it is desirable to provide a sealed system in which the contents are retained inside prior to use.

In addition, it is desirable that the system provide some indication as to whether it has been opened, alerting users to the potential that some of the contents may have been spilled or otherwise depleted.

One possible approach is to provide a dispenser cap that protects the contents of the system prior to use or that regulates access to the contents during use, or both. Many attempts have been made to develop child-resistant or tamper-evident dispenser caps for use with various products.

U.S. Pat. No. 5,121,859 ("the '859 patent") to G. Stull, entitled "Non-resealable Dispenser Cap Construction", shows a non-resealable dispenser cap for use with hand-held dispensers. The cap has an elongated tapered, stepped hollow spout with a discharge orifice. A closure cap having a transverse closure wall is mounted on the spout. The transverse wall engages and closes over the discharge orifice. With the closure cap so mounted, the transverse closure wall is distorted and biased by its engagement with the wall of the discharge orifice. Either the closure cap or the spout is formed with two oppositely-disposed frangible tabs which overlie and are permanently attached to the other. Each tab has a zone of weakness that can be readily ruptured by rotating either the cap or the spout.

U.S. Pat. No. 2,930,063 ("the '063 patent") to M. Stull, entitled "Dispensing Cap for Containers", shows a flexible plastic applicator cap for use with small hand-held containers. The cap has a body adapted to be attached to the container. A hollow, cylindrical spout is integral with and extends an appreciable distance from the body. The tip of the spout has a transversely disposed, annular, external end face making an acute angle with the spout's axis, having a discharge orifice surrounded by the surface of the end face and having a stopper formed with walls of reduced thickness at its base. The walls are integral with the spout and project from the end face thereof. The cap may be readily cut or torn. Thereby, the stopper (at the reduced walls thereof) is severed from the spout to reveal the discharge orifice. The stopper has an extremity of reduced diameter for closing the orifice.

U.S. Pat. No. 3,083,858 ("the '858 patent") to Biedenstein, entitled "Tear Type Container Closure", shows a container closure which is integrally connected to the container by a frangible connection. The closure may be separated from the container by a pull on the closure. This tears the frangible connection, but leaves a major portion of the material of the frangible connection attached either to the closure or the container where it will be active as a temporary resealing means between the closure and the container.

U.S. Pat. No. 4,757,911 ("the '911 patent") to Larkin et al., entitled "Container and Closure Construction", shows a thin flexible fluid-tight cover of PVC bonded to a rigid port of a diluent container for use in medicinal applications and which is to be subjected to heat sterilization. The cover includes an outer flange for bonding to a complementary surface around the port, and a removable section for spanning the port. The removable section includes a central flexible diaphragm and a cylindrical wall. The diaphragm is axially expandable by flexing of an annular convolution. A frangible tear line joins the cylindrical wall to the outer flange. The cylindrical wall is disposed adjacent the outer surfaces of an abutment wall on the port to provide stress relief against rupture of the tear line from stresses generated in the cover during sterilization. A pull ring attached to a narrow post is located adjacent the wall for concentrating manual pulling forces to a limited segment of the tear line.

U.S. Pat. No. 5,249,695 ("the '695 patent") to Luch et al., entitled "Spout Fitment Closure Plug", shows a spout fitment adapted to be attached to and surround a hole in a container, particularly a paperboard carton or other flexible container. The spout fitment has internal threads and an external flange which seals around the hole and is fixed to the container by thermal means, adhesive or the like. A cap has a top disk from which an externally threaded skirt depends. The lower edge of the skirt seals against a sealing membrane on the spout. Surrounding the skirt is a tamper-evident band attached to the lower edges of gripping ribs by frangible bridges. The tamper-evident band has a locking device engaging a complementary locking device on the fitment. Thus, the cap cannot be unscrewed without removing the tamper-evident band.

U.S. Pat. No. 5,201,440 ("the '440 patent") to Gross, entitled "Closure with Tamper-evident Tear-off Panel with a Flow Control Element", shows a container closure which includes a body for mounting on the container. The body defines a dispensing orifice. A flow control device, such as a lid, is disposed on the body and moved between positions opening and closing the dispensing orifice. A tamper-indicating member is connected by a first frangible web to the lid. An anchor is connected with a second frangible web to another portion of the tamper-indicating member, and the anchor is retained by the closure body. The tamper-indicating member also includes a graspable pull tab, which can be pulled to completely sever the frangible webs, permitting the lid to be opened while providing evidence of tampering with the closure.

A problem with these cap configurations, however, is that they are not particularly suited for use with a liquid emanation system which employs a wick. Nor do they provide "child-resistant" or "spill-resistant" closures for such wick-based liquid emanation systems.

Additionally, the foregoing configurations do not address a further problem which is often encountered with such wick-based liquid emanation systems, namely, the condensation that can accumulate on the heating mechanism and other parts of the system due to excess emanation. If the wick extends a considerable length above the liquid, emanation will occur over the entire length, often leading to condensation of excess moisture on the heating device and the remainder of the system, which is inconvenient and can be potentially damaging. One possible solution to this problem would be to limit the length by which the wick extends from the liquid. However, if the wick only extends slightly above the surface of the liquid, then it becomes very difficult to heat the wick without heating the liquid reservoir as well. This can lead to additional problems such as direct evaporation of the liquid.

Accordingly, there is a need for a wick-based liquid emanation system, and for a closure for use with a wick-based liquid emanation system, which overcome these and other drawbacks.

There is also a need to provide a closure for use with a wick-based liquid emanation system that is particularly suited to resist tampering or access by children. (Hereinafter, a wick-based liquid emanation system and closure therefor will collectively be referred to as a "system.")

There is a further need for such a system which indicates whether the system has been opened.

There is yet another need in the art for such a system which controls the rate of liquid emanation from the system.

There is an additional need in the art for such a system which can be inexpensively manufactured.

SUMMARY OF THE INVENTION

The present invention has been made in consideration of the above-described problems in the prior art.

An object of the present invention is to provide an improved wick-based liquid emanation system including a low cost, child resistant closure for such a wick-based liquid emanation system.

An additional object of the invention is to provide such a system which provides an indication as to whether the system has been opened.

A further object of the invention is to provide such a system that reduces condensation of product from the wick onto other parts of the system.

Yet another object of the invention is to provide such a system which provides for the retention of the wick within the system, to prevent access to the contents thereof.

According to one aspect, the present invention provides a child-resistant, wick-based liquid emanation system including a container capable of containing liquid and having an opening. A wick is partially disposed within the container and has an extended portion extending through the opening of the container. A hollow overcap encases the extended portion of the wick and has a closed, separable tip and an open base. The base is attached to the container to cover the opening. The system is activated by separating the tip from the overcap.

A retainer may be provided for obstructing complete removal of the wick from the container through the overcap after the tip is separated from the overcap. The retainer can include a shoulder disposed in the overcap between the tip and the base for retaining the wick toward the base of the overcap. Alternatively, the retainer can include a protrusion protruding from the wick for engaging at least one of an inner surface of the overcap and an inner surface of the container.

The overcap can have a frangible portion located near its tip facilitating separation of the tip from the overcap, and the wick can extend from within the container past the frangible portion toward the tip. The wick may be formed with the protrusion unitary therewith.

According to another aspect of the present invention, a child-resistant, wick-based liquid emanation system includes a container capable of containing liquid, a hollow spout protruding from the container and having a closed, separable tip, and a wick partially disposed within the container and having an extended portion extending into the spout. The system is activated by separating the tip from the spout.

According to yet another aspect of the present invention, a child-resistant overcap is provided for use with a wick-based liquid emanation system, the system including (i) a container having an opening and (ii) a wick partially disposed within the container and having an extended portion extending through the container opening. The overcap includes a closed, separable tip, an open base attachable to the container to cover the container opening, and a shoulder disposed between the tip and the base. The overcap encases the extended portion of the wick when the base is attached to the container, and the shoulder retains the wick toward the base of the overcap. The system is activated by separating the tip from the overcap.

According to still another aspect of the present invention, a child-resistant overcap is provided for use with a wick-based liquid emanation system including (i) a container having an opening and (ii) a wick partially disposed within the container and having an extended portion extending through the container opening. The overcap includes a closed, separable tip and an open base which is attachable to the container to cover the container opening. The overcap encases the extended portion of the wick when the base is attached to the container. A retainer is provided for obstructing complete removal of the wick from the container through the overcap after the tip is separated from the overcap.

This brief summary of the invention has been provided so that the nature of the invention may be generally understood. However, this summary should not be construed to limit the invention.

The foregoing and other objects, aspects, features and advantages of the present invention will become apparent from the following detailed description of the preferred embodiments taken in conjunction with the accompanying drawings.

BRIEF DESCRIPTION OF THE DRAWINGS

Like reference numerals have been used for like or similar elements throughout the views.

DESCRIPTION OF THE PREFERRED EMBODIMENTS

Figure 1:
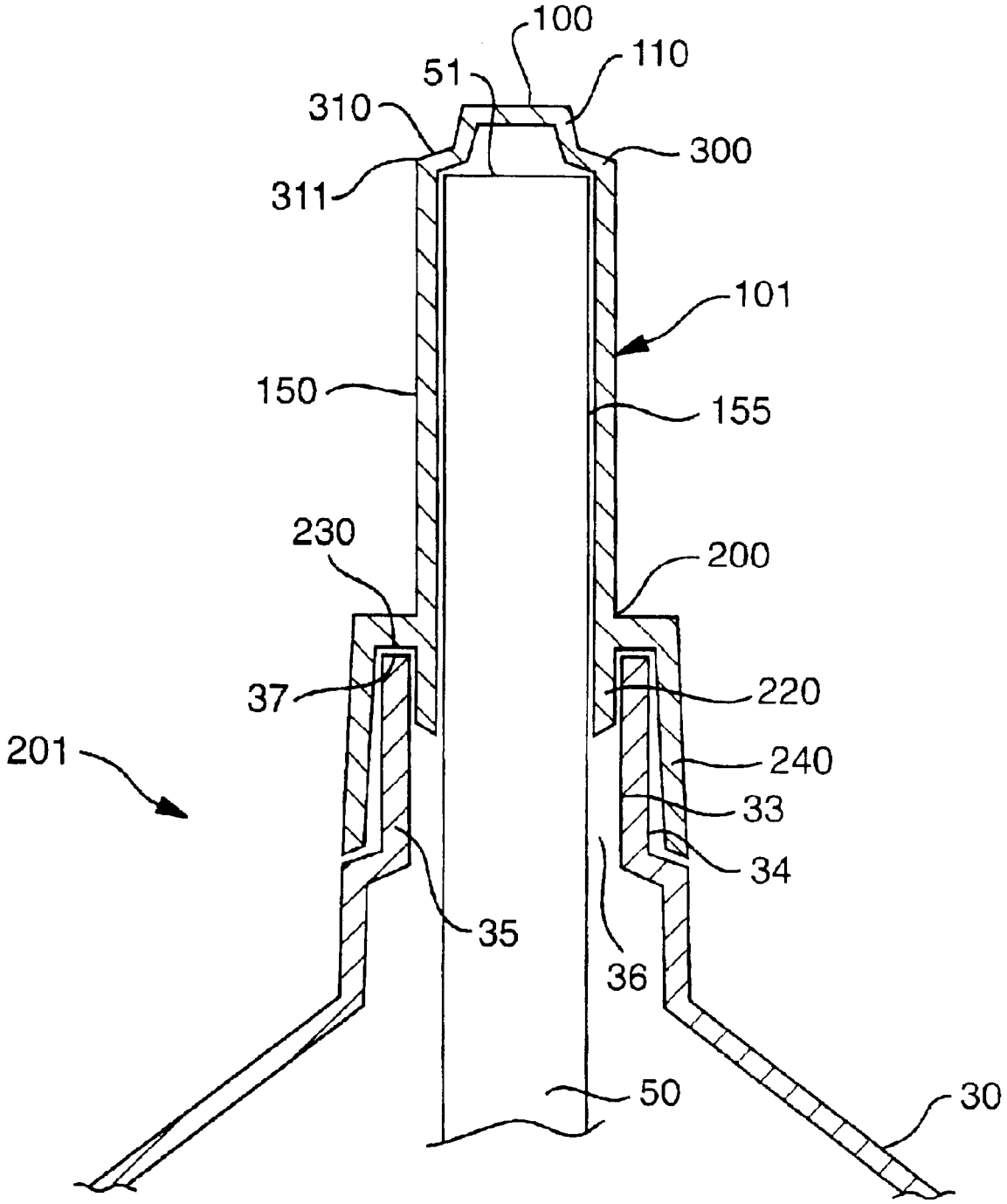
FIG. 1 is a partial cross-sectional view, in elevation, of a first preferred embodiment of the wick-based emanation system with child-resistant overcap of the present invention.

FIG. 1 shows a partial cross-sectional view, in elevation, of a first preferred embodiment of the wick-based liquid emanation system 201 of the present invention. Liquid emanation system 201 includes a container 30 for containing a liquid (not shown) to be dispersed, a wick 50 partially disposed in container 30 and an overcap 101 secured to container 30. These features will be discussed in more detail below.

One end (not shown) of the wick 50 is partially submerged in the liquid to be emanated. The shape of the container 30 is not an essential feature of the invention. Therefore, the portion of the container 30 containing the liquid is not shown in detail in the drawing. The other end of wick 50 extends out through an opening 36 in the container 30. In this embodiment, the container 30 has a neck 35 through which the opening 36 is disposed.

In this embodiment, the overcap 101 is shown having a generally circular cross section, and is secured to the neck 35 of the container 30, as will be discussed in more detail below. Of course, the overcap 101 need not be generally circular in cross section. Rather, other geometrical shapes can be used as desired. Nevertheless, for the purposes of conciseness and clarity, the overcap 101 will be described as being circular in cross section, with reference to such features as its "diameter" and "circumference."

The overcap 101 encases a portion of the wick 50 which extends through the opening 36. The tip 100 of the overcap 101 is closed. The base 200 of the overcap 101 is secured to the container neck 35. Between the tip 100 and the base 200, wall 150 of the overcap 101 defines a cavity 155 which preferably, but not necessarily, conforms closely to the shape and size of the wick 50, so that it closely encases the wick 50.

In this embodiment, overcap 101 includes a shoulder 300 provided near the tip 100. The shoulder 300 defines a reduction in the diameter of the cavity 155. A transverse wall 310 extends partially inward from the wall 150 to effect this reduction in diameter. This transverse wall 310 acts as a barrier, for reasons that will be made apparent later, against movement of the wick 50 by some external force past the shoulder 300 toward the tip 100.

Extending from the tip 100 to the transverse wall 310 is a skirt 110. The skirt 110 is shown as having a larger diameter adjacent the shoulder 300 than it does adjacent the tip 100. However, the skirt 110 can increase, decrease, or remain constant in diameter from the shoulder 300 to the tip 100 depending on the relative dimensions of the tip 100 and the shoulder 300. Additionally, the skirt 110 and transverse wall 310 need not be separate elements, but can be combined. If this is the case, the combination skirt/transverse wall should decrease in diameter as it approaches the tip 100 in order to provide the barrier past which the wick 50 cannot be moved without considerable effort. Alternately, the transverse wall 310 can be provided as a cantilever-like barrier, and the skirt 110 can extend from the outer perimeter 311 of the transverse wall 310. In this case, the transverse wall 310 can be formed in any number of shapes to effect a localized reduction in diameter of the cavity 155 past which the wick 50 cannot be moved without considerable effort.

In the embodiment of FIG. 1, the base 200 of overcap 101 is provided with an inner flange 220 and an outer flange 240 for securing the overcap 101 to the container 30. The inner flange 220 engages inner wall 33 of the container neck 35. The outer flange 240 engages outer wall 34 of the container neck 35. Together, the inner and outer flanges 220, 240 define a seat 230 into which mouth 37 of the container 30 fits. In this embodiment, the mouth 37 and seat 230 can be welded, fused, or otherwise permanently bonded together to provide a sealed engagement. While it is preferred that the base 200 be fixed in engagement to the neck 35, this particular means of engagement is not critical to the invention. The base 200 and neck 35 can be engaged by any of a number of means, some of which will be discussed in more detail later.

In this embodiment, the overcap 101 seals the wick 50 and liquid contents of the system 201 within the container 30. In order to activate the system 201, i.e., permit dispersal of the liquid into the surrounding atmosphere, the tip 100 is separated from the overcap 101. For example, the tip 100 can be separated by cutting through the skirt 110. This feature of the invention (the separation of the tip 100) can be accomplished in other ways. For example, a groove (not shown) can be provided in the skirt 110 to create a localized weakness in the overcap 101. In that case, the tip 110 can be removed by tearing the overcap 101 at this weakened groove. Alternatively, the tip 100 can be a separate piece, adhesively affixed to close the end of the overcap 101. In that case, the system 201 would be activated by peeling off or otherwise removing the tip 100 from the overcap 101. These and other equivalent ways to secure the tip 100 to overcap 101 can be utilized within the concepts of the present invention.

In any of these embodiments, once the tip 100 is removed, an opening is created in the overcap 101 through which the distal end 51 of the wick 50 is exposed. Now, however, the shoulder 300 of overcap 101 acts as a retainer against removal of the wick 50. It is preferred that the wick 50 not pass by the shoulder 300 toward the newly-formed opening in the overcap 101.

Once the tip 100 has been separated, heat can be applied to the portion of the wick 50 within the overcap 101 by means of a localized heat source (not shown), preferably but not necessarily in the form of a ring-shaped heating element (not shown) which encircles the overcap 101. Wick 50 disperses liquid to the surrounding atmosphere, which in turn allows additional liquid to enter the wick from the container.

In addition to securing the wick 50, the overcap 101 acts to reduce the delivery rate of molecularized liquid into the air. By permitting emanation to occur primarily through the distal end 51 of the wick 50, instead of throughout the entire length of wick 50, liquid residue is less likely to condense on the heating mechanism and other internal surfaces of the system 20.

Figure 2A:
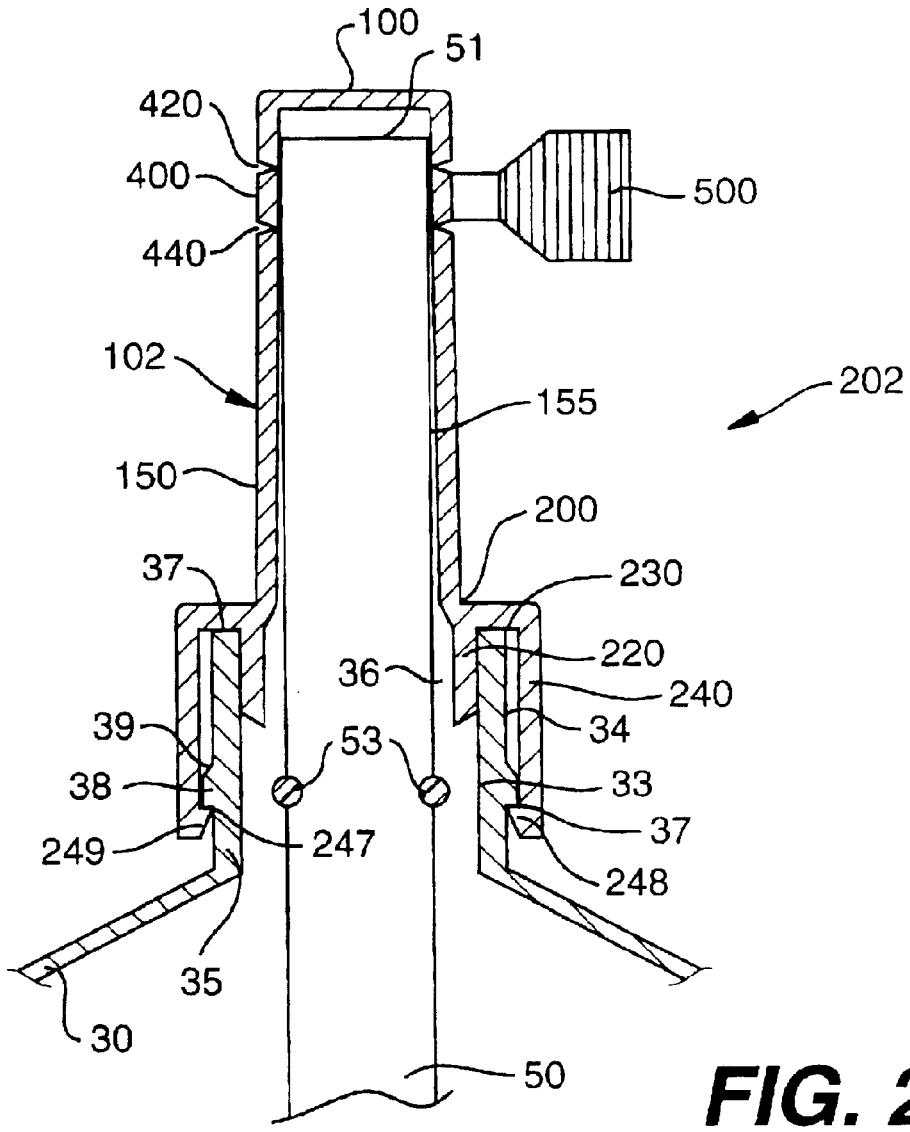
FIG. 2A is a partial cross-sectional view, in elevation, of a second preferred embodiment of the wick-based emanation system with child-resistant overcap of the present invention.
Figure 2B:
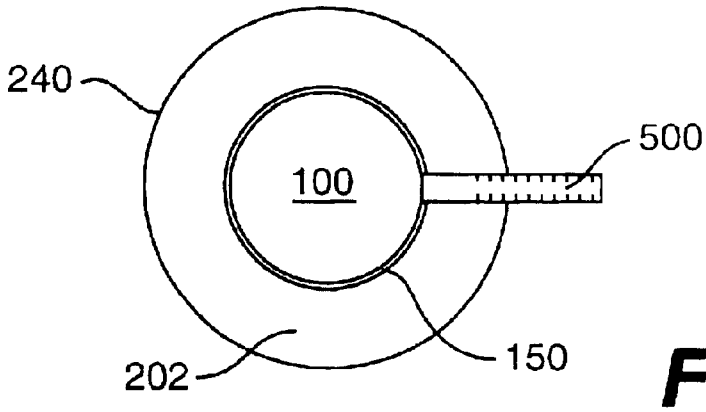
FIG. 2B is a plan view of the second preferred embodiment of the present invention.

In some cases, it may be desirable to provide for a greater rate of emanation. An alternate embodiment of the wick-based liquid emanation system with child-resistant overcap of the present invention is shown in FIGS. 2A and 2B. Reference should be made to the discussion of FIG. 1 above for a detailed description of like elements from the first embodiment. A major difference between the second embodiment and the first embodiment is that, in the second embodiment, the wick 50 extends from overcap 102 once the tip 100 is removed.

In the second embodiment, it is preferred that the tip 100 not be separated from the overcap 102 by cutting, because the wick 50 could be cut as well. Therefore, in this embodiment, wall 150 is provided with a frangible portion 400, in this case defined by a pair of substantially parallel, V-shaped grooves 420 and 440. It is preferred that the distal end 51 of the wick 50 extend beyond this frangible portion 400 toward the tip 100.

In this embodiment, as in the previous one, system 202 is activated by removal of the tip 100. In this case, the removal is accomplished by tearing the tip 100 off of the overcap 102 at the frangible portion 400. The wick 50 will extend out from the overcap 102, which is now open at the frangible portion 400, to allow greater wicking action to occur due to the additional wick exposure. In order to facilitate the removal of the tip 100, a tab 500 may be provided, extending from the wall 150 between the grooves 420, 440. This allows the user to grasp the tab 500 and pull to effect the tearing of the frangible portion 400. Tab 500, attached to wall 150, is shown in more detail in FIG. 2B.

In this embodiment, because there is no shoulder to act as a retainer, it may be desired to provide an alternate form of retainer for obstructing the removal of the wick 50 through the overcap 102 once the tip 100 is separated. This would reduce the likelihood that a child could remove the wick 50 and access the liquid. It would also minimize the amount of spillage that would occur should the system 202 be accidentally tipped. This can be done by several means. If the wick 50 is straight and of conventional construction, i.e., bonded polyester, cellulose, or the like, an external mechanical retainer can be employed. For example, a pin (not shown) can be inserted through the wick 50, so that it protrudes from the wick 50 and the combination cannot fit through the overcap 102 or the container opening 36. Alternatively, a clamping collar 53 or the like can be provided, as shown, as a protrusion for the same purpose. Clamping collar 53 can be secured to wick 50 in any desired manner.

Also, as an alternative to the arrangement discussed above, this embodiment and the ones discussed below employ various "stake-on" or "snap-fit" methods of engaging the overcap 102 and the container 30. The method used in this embodiment will now be discussed.

Outer flange 240 of base 200 is provided with an inwardly-depending pawl 248. This pawl 248 engages with container lip 38 which protrudes from the container neck 35. Preferably the lip 38 and pawl 248 extend fully around the perimeters of the neck 35 and outer flange 240, respectively. The lip 38 and the pawl 248 are respectively provided with a tapered leading edge 39, 249 and a flat trailing edge 37, 247. Therefore, when the overcap 102 is brought into engagement with the container 30, the leading edge 39 of the lip 38 initially engages the leading edge 249 of the pawl 248. This engagement of these tapered surfaces 39, 249 causes the outer flange 240 to deform outwardly, allowing the pawl 248 to slip past the lip 38. The pawl 248 snaps behind the lip 38, so that the trailing edge 37 of the lip 38 engages the trailing edge 247 of the pawl 248.

Figure 3A:
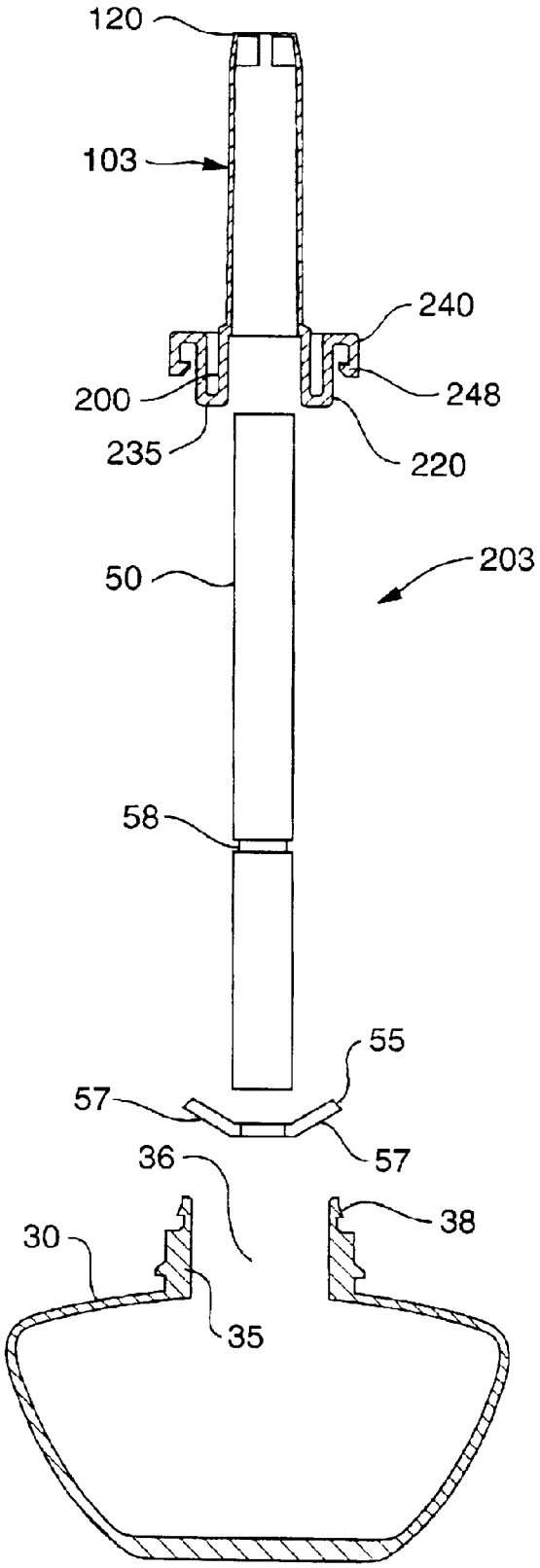
FIG. 3A is an exploded cross-sectional view, in elevation, of a third preferred embodiment of the present invention.
Figure 3B:
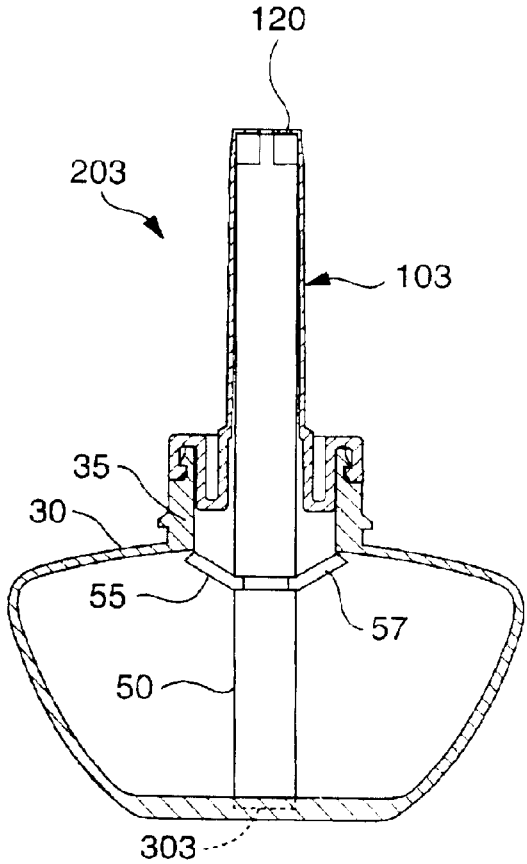
FIG. 3B is a cross-sectional view, in elevation, of the embodiment shown in FIG. 3A, as assembled.

In another embodiment, shown in the exploded cross-sectional view of FIG. 3A, in order to securely retain the wick 50 while facilitating the loading of the wick 50 through the container opening 36, a flexible collar 55 is provided. Collar 55 can have flexible wings 57 which angle upward and can be flexed upward against the wick 50. Thus, upon insertion, the wings 57 will elastically collapse against the wick 50 to permit the wick 50 and collar 55 to be inserted through the container opening 36 into the container 30. Once entirely through the container opening 36, the wings 57 will open and engage the inside of either the container 30 or the overcap 103, as shown in FIG. 3B, obstructing the removal of the wick 50. To increase the integrity of this design, a circumferential groove 58 can be cut out of the wick 50 to provide a seat for the collar 55. Collar 55 can be made of flexible metal or plastic, for example, to facilitate installation. FIG. 3B also shows an optional recess 303 in the container 30 for receiving wick 50.

FIGS. 3A and 3B illustrate an additional feature that can be provided with any of the embodiments. In these figures, the tip 100 (see FIGS. 1, 2A and 2B) has already been removed from the overcap 103. Instead of merely leaving behind an opening through which the wick 50 extends, in this embodiment, a pervious cage 120 closely encases the extended portion of the wick 50. This assists in retaining the wick 50. When cage 120 is utilized, it is preferred, for simplicity of construction, that the tip 100 of the overcap 103 be a separate piece adhesively affixed to or sealed over the cage 120, so that it can be peeled or otherwise readily removed from the overcap 10 to activate the system 20. The tip 100 alternatively could be integrally formed with the overcap 103, so that the tip 100 is a separate layer which encases the cage 120, and the overcap 103 can be provided with a frangible portion at which the tip 100 can be separated therefrom.

This embodiment employs a variation of the earlier-described "stake-on" method of engagement between the overcap 103 and the container 30. Similar to the arrangement discussed with respect to the embodiment shown in FIG. 2A, the outer flange 240 of the overcap 103 is provided with an inwardly-depending pawl 248. The container 30 is provided with a corresponding lip 38, which engages the pawl 248 in a similar manner to the earlier embodiment. In this embodiment, however, the inner flange 220 does not depend downwardly from the base 200. Instead, the inner flange 220 extends upwardly from a spacer ring 235, which extends out from the base 200. By spacing the inner flange 220 from the base 200, the overcap 103 can sit within the container neck 35, as shown in FIG. 3B. This arrangement permits the container neck 35 to have a substantially larger cross section than the wick 50, making it much easier to insert the wick 50 and overcap 103 into the container neck 50.

Figure 4A:
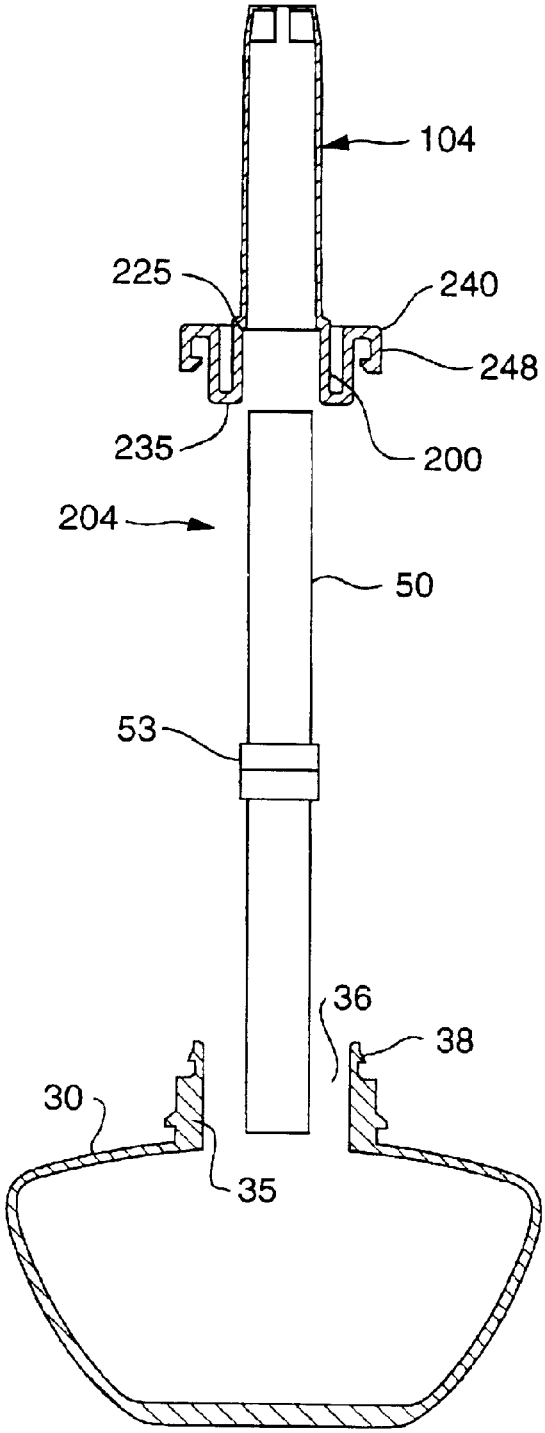
FIG. 4A is an exploded, cross-sectional view, in elevation, of a fourth preferred embodiment of the present invention.

In yet another embodiment, shown in the exploded cross-sectional view of FIG. 4A, a protrusion or collar 53 may be formed integrally with a wick 50 itself. By way of example, this can be accomplished by molding a wick 50 with an integral collar 53.

In the present invention, the preferred method of molding the wick 50 is sintering. In this method, a suitable powdered plastic, such as ultra-high molecular weight polyethylene or polypropylene, is lightly packed into a mold. This packing can be accomplished by light pressure or vibration or any other suitable means. The packed mold is then heated to a temperature which is sufficient to allow the plastic to bond together, but not sufficient to liquefy the plastic to such an extent that it can flow. This results in a solid piece which is porous and therefore wicks liquid. A wick of such construction can be molded into a variety of shapes. In addition, an overcap [10] for use with such a wick can be formed to have a shape conforming thereto.

Figure 4B:
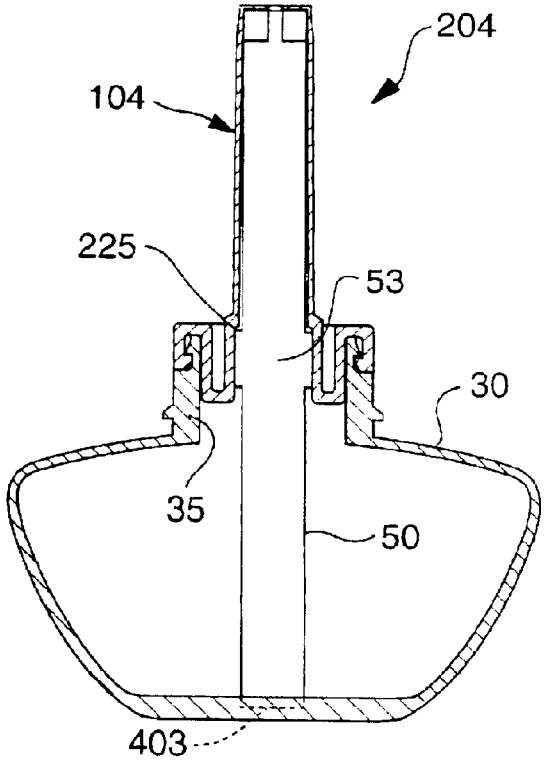
FIG. 4B is a cross-sectional view, in elevation, of the embodiment shown in FIG. 4A, as assembled.

Referring back to FIG. 4A, in this embodiment, overcap 104 is provided with an inner step 225. As can be seen in FIG. 4B, the step 225 engages the collar 53 when system 204 is assembled, retaining the wick 50 in the container 30. It should be noted that, using this method, the wick 50 alternatively could be molded with a groove for use as a seat for a separate winged collar such as described above with respect to the FIGS. 3A and 3B.

A variation of the embodiments shown in FIGS. 2A through 4B is one in which only a single flange is provided, which engages the container neck 35. This single flange may snugly fit either over or within the container neck 35. Further, although a "stake-on" arrangement has been shown in the preceding embodiments, other methods may be utilized to secure a respective overcap to container 30. For example, frictional securement, various mechanical interlocking arrangements, chemical bonding, or heat welding may be utilized. It is preferred, however, that the engagement be such that the respective overcap cannot be removed without considerable force or effort.

Of course, it is not a necessary feature of the invention that the container 30 have a neck 35. If no neck is provided, a respective overcap can be affixed directly to the mouth 37 of the opening 36 of the container 30 in a manner similar to those described above.

It is also possible that an overcap can be integrally formed with the container 30. If this is the case, the container/overcap is formed with a temporary orifice for filling and loading. The liquid is added, and the wick is loaded into place. At this point, the orifice is sealed, closing the system. Such a system could be configured according to any of the embodiments described above.

In each of the embodiments discussed above, for cost effectiveness, a respective overcap is preferably formed by injection molding. In general, an overcap is preferably made of a thermoplastic or other material which has a high enough heat index to withstand heating and is impervious to chemical attack from the liquid used in the emanation system. In the case of a snap-fit or similar engagement mechanism, the material should provide sufficient flexibility to permit engagement. The particular application of the system will dictate which specific material is best.

If the system is being used to emanate an air freshener, then the wick 50 will need to be exposed to temperatures on the order of approximately 60° C. Polyethylene is particularly well-suited for this, especially with respect to the embodiments in which a tip is tom from an overcap at a localized weakness, because this thermoplastic has less tensile strength and tears more easily than most.

On the other hand, materials such as nylon, polypropylene or other thermoplastics with higher heat indexes will be better suited for higher-temperature applications. For example, if the system is being used to emanate an insect repellant, temperatures closer to or exceeding 120° C. may be necessary for proper wicking.

INDUSTRIAL APPLICABILITY

The wick-based liquid emanation system and overcap of the present invention can be used wherever it is desired to molecularize and disperse a liquid into the atmosphere via a wicking mechanism. For instance, the system and overcap can be used in such varied applications as dispersal of insect repellent or air freshener, for example, into the air.

Although specific embodiments of the present invention have been described in detail, it will be understood that this description is merely for purposes of illustration. Various modifications of and equivalent structures corresponding to the disclosed aspects of the preferred embodiments in addition to those described above may be made by those skilled in the art without departing from the spirit of the following claims. For example, those of ordinary skill in the art will appreciate that certain variations in the size, shape, number, arrangement, and material of various portions of the disclosed system and overcap may be made without departing from the spirit of the invention. Accordingly, the scope of the invention defined by the following claims should be accorded the broadest reasonable interpretation so as to encompass such modifications and equivalent structures.

What is claimed is:

1. A child-resistant, wick-based liquid emanation system comprising:

a container capable of containing liquid, said container having an opening;

a wick partially disposed within said container and having an extended portion extending through the opening of said container; and a hollow overcap encasing the extended portion of said wick, said overcap having (i) a closed tip, separable from the overcap, and (ii) an open base, the base being attached to said container to cover the opening, said overcap closely conforming to the shape and size of said wick, wherein said system is activated by separating the tip from said overcap.

2. The system of claim 1, further comprising a retainer for obstructing complete removal of said wick from said container through said overcap after the tip is separated from said overcap.

3. The system of claim 2, wherein the retainer comprises a shoulder disposed in said overcap between the tip and the base for retaining said wick toward the base of said overcap.

4. The system of claim 2, wherein said retainer comprises a protrusion protruding from said wick for engaging at least one of an inner surface of said overcap and an inner surface of said container.

5. The system of claim 4, wherein said overcap has a frangible portion located near the tip, the frangible portion facilitating separation of the tip from said overcap.

6. The system of claim 5, wherein said wick extends from within said container past the frangible portion toward the tip.

7. The system of claim 6, wherein:

said container has a neck through which the opening is disposed, and said overcap has a flange depending from the base which engages the neck of said container.

8. The system of claim 7, wherein the neck of said container and the flange of said overcap have corresponding protrusions which interact to lock the base of said overcap to said container.

9. The system of claim 4, wherein said wick is formed with said protrusion unitary therewith.

10. The system of claim 9, wherein:

said container has a neck through which the opening is disposed, and said overcap has a flange depending from the base which engages the neck of said container.

11. The system of claim 10, wherein the neck of said container and the flange of said overcap have corresponding protrusions which interact to lock the base of said overcap to said container.

12. A child-resistant, wick-based liquid emanation system comprising:

a container capable of containing liquid;

a unitary, hollow spout projecting from said container, said spout having a closed tip, separable from the spout; and a wick partially disposed within said container and having an extended portion extending into said spout, said spout closely conforming to the shape and size of said wick, wherein said system is activated by separating said tip from said spout.

13. The system of claim 12, further comprising a retainer for obstructing complete removal of said wick from said container through said spout after the tip is separated from said spout.

14. The system of claim 13, wherein the retainer comprises a shoulder disposed in said spout between the tip and said container, the shoulder retaining said wick toward said container.

15. The system of claim 13, wherein the retainer comprises a protrusion protruding from said wick for engaging at least one of an inner surface of said spout and an inner surface of said container.

16. The system of claim 15, wherein said spout has a frangible portion located near said tip, said frangible portion facilitating separation of said tip from said spout.

17. The system of claim 16, wherein said wick extends from within said container past said frangible portion toward said tip.

18. The system of claim 15, wherein said wick is formed with said protrusion unitary therewith.

19. The system of claim 13, wherein said wick has a circumferential groove on a portion thereof which is disposed within said container, and wherein said retainer comprises:

a collar seated in the groove of said wick; and a wing extending from said collar for engaging at least one of an inner surface of said spout and an inner surface of said container.

20. The system of claim 19, wherein said wing is elastically foldable against said wick toward the extended portion of said wick to facilitate insertion into said container of the portion of said wick at which said wing extends from said collar.

21. A child-resistant overcap for use with a wick-based liquid emanation system, the system including (i) a container having an opening and (ii) a wick partially disposed within the container and having an extended portion extending through the container opening, said overcap comprising:

a closed tip, separable from the overcap;

an open base being attachable to the container to cover the container opening, wherein said overcap encases the extended portion of the wick when said base is attached over the container opening, said overcap closely conforming to the shape and size of said wick; and a retainer for obstructing complete removal of the wick from the container through said overcap after said tip is separated from said overcap.

22. The overcap of claim 21, wherein said retainer comprises a pervious cage, and said tip is removably attached to said cage.

23. The overcap of claim 21, wherein the wick has a protrusion, and said retainer comprises an inner surface of said overcap for engaging the protrusion.

24. The overcap of claim 23, wherein said overcap has a frangible portion located near said tip, said frangible portion facilitating separation of said tip from said overcap.

25. The overcap of claim 24, wherein the container has a neck through which the opening is disposed, and said base has a flange which is attachable to said neck.

26. The overcap of claim 25, wherein said flange and the container neck have corresponding protrusions which interact to lock said base to the container.

27. The overcap of claim 21, wherein said retainer comprises a shoulder, disposed between said tip and said base, which retains the wick toward said base.

28. The overcap of claim 27, wherein the container has a neck through which the opening is disposed, and said base has a flange which is attachable to said neck.

29. The overcap of claim 28, wherein said flange and the container neck have corresponding protrusions which interact to lock said base to the container.

*30. A wick-based liquid emanation system comprising:*

*a container capable of containing liquid, the container having an opening;*

*a wick partially disposed within the container and having an extended portion extending through the opening of the container; and*

*an overcap including:*

*(i) a pervious cage encasing the extended portion of the wick, the pervious cage having (a) an open base portion that is attached to the container to cover the opening, and (b) a distal portion, opposite from the base portion, having an opening through which the wick can be exposed to the atmosphere, the pervious cage having an interior surface that closely conforms to the shape and size of the wick; and*

*(ii) a closed tip covering at least the opening in the distal portion of the pervious cage, the closed tip being separable from the overcap to expose the wick to the atmosphere,*

*wherein the system is activated by separating the closed tip from the overcap.*

*31. The overcap of claim 30, wherein the closed tip encases the pervious cage.*

*32. The overcap of claim 30, wherein the closed tip is removably attached to the pervious cage.*

*33. The overcap of claim 30, wherein the wick has a protrusion, and the interior surface of the pervious cage engages the protrusion.*

*34. A wick-based liquid emanation system comprising:*

*a container capable of containing liquid;*

*a unitary, hollow spout projecting from the container, the spout having a distal portion with an opening therein;*

*a closed tip, covering at least the opening in the distal portion of the spout, the closed tip being separable from the spout; and*

*a wick partially disposed within the container and having an extended portion extending into the spout, the spout having an interior surface closely conforming to the shape and size of said wick,*

*wherein the system is activated by separating the tip from the spout, thereby exposing the wick to the atmosphere through the opening in the distal portion of the spout.*

*35. The system of claim 34, wherein the closed tip encases the spout.*

*36. The system of claim 34, wherein the closed tip is removably attached to the spout.*

*37. The overcap of claim 34, wherein the wick has a protrusion, and the interior surface of the spout engages the protrusion.*

*38. An overcap for use with a wick-based liquid emanation system, the system including (i) a container having an opening and (ii) a wick partially disposed within the container and having an extended portion extending through the container opening, the overcap comprising:*

*a pervious cage encasing the extended portion of the wick, the pervious cage having (i) an open base portion that is attached to the container to cover the container opening, and (ii) a distal portion, opposite from the base portion, having an opening through which the wick can be exposed to the atmosphere, the pervious cage having an interior surface that closely conforms to the shape and size of the wick; and*

*a closed tip covering at least the opening in the distal portion of the pervious cage, the closed tip being separable from the overcap to expose the wick to the atmosphere,*

*wherein, when the closed tip is separated from the overcap, the pervious cage obstructs complete removal of the wick from the container through the opening in the distal portion of the pervious cage.*

*39. The overcap of claim 38, wherein the closed tip encases the pervious cage.*

*40. The overcap of claim 38, wherein the closed tip is removably attached to the pervious cage.*

*41. An overcap for use with a wick-based liquid emanation system, the system including (i) a container having an opening and (ii) a wick partially disposed within the container and having an extended portion extending through the container opening, the overcap comprising:*

*an open base attachable to the container to cover the container opening;*

*a sheath extending from the base and having an end opposite to the base to define a cavity that closely conforms to the shape and size of the wick, the sheath encasing the extended portion of the wick when the base is attached to the container to cover the container opening;*

*a closed closure member separable from the overcap to expose the wick to the atmosphere through the end of the cavity; and*

*a retainer for obstructing complete removal of the wick from the container through the sheath when the closure member is separated from the overcap.*

*42. The overcap of claim 41, wherein the closed closure member encases the sheath.*

*43. The overcap of claim 41, wherein the closed closure member is removably attached to the sheath.*

*44. A wick-based liquid emanation system comprising:*

*a container capable of containing liquid, the container having an opening;*

*a wick partially disposed within the container and having an extended portion extending through the opening of the container; and*

*an overcap including:*

*(i) a pervious cage encasing the extended portion of the wick, the pervious cage having (a) an open base portion that is attached to the container to cover the opening, and (b) a distal portion, opposite from the base portion, having an opening through which the wick can be exposed to the atmosphere, the pervious cage having an interior surface that closely conforms to the shape and size of the wick; and*

*(ii) a sealing structure that encases the pervious cage, the sealing structure being separable from the overcap to expose the wick to the atmosphere,*

*wherein, when the sealing structure is separated from the overcap, the pervious cage prevents complete removal of the wick from the container through the opening in the distal portion of the pervious cage.*

* * * * *